United States Patent
Lundahl

(10) Patent No.: US 9,597,150 B2
(45) Date of Patent: Mar. 21, 2017

(54) METHOD FOR THE PERMANENT REMOVAL OF HAIR

(71) Applicant: DUSA PHARMACEUTICALS, INC., Wilmington, MA (US)

(72) Inventor: Scott Lundahl, Wilmington, MA (US)

(73) Assignee: DUSA PHARMACEUTICALS, INC., Wilmington, MA (US)

(*) Notice: Subject to any disclaimer, the term of this patent is extended or adjusted under 35 U.S.C. 154(b) by 418 days.

(21) Appl. No.: 14/011,858

(22) Filed: Aug. 28, 2013

(65) Prior Publication Data

US 2014/0074075 A1    Mar. 13, 2014

Related U.S. Application Data

(60) Provisional application No. 61/698,976, filed on Sep. 10, 2012.

(51) Int. Cl.
| | |
|---|---|
| *A61B 18/18* | (2006.01) |
| *A61B 18/20* | (2006.01) |
| *A61N 5/06* | (2006.01) |
| *A61B 18/00* | (2006.01) |

(52) U.S. Cl.
CPC ............ *A61B 18/18* (2013.01); *A61B 18/203* (2013.01); *A61N 5/062* (2013.01); *A61B 2018/00476* (2013.01); *A61N 5/0617* (2013.01); *F04C 2270/0421* (2013.01)

(58) Field of Classification Search
CPC ...................................... A61B 18/18
USPC .......................... 606/2, 9–19; 607/80, 88–95
See application file for complete search history.

(56) References Cited

U.S. PATENT DOCUMENTS

| | | |
|---|---|---|
| 5,669,916 A | 9/1997 | Anderson |
| 6,050,990 A | 4/2000 | Tankovich et al. |
| 2002/0062835 A1 | 5/2002 | Yano et al. |
| 2007/0154536 A1 | 7/2007 | Sumian |

FOREIGN PATENT DOCUMENTS

EP    1312353    5/2003

OTHER PUBLICATIONS

Sato, et al. "Effect of Adenovirus-Mediated Expression of Sonic Hedgehog Gene on Hair Regrowth in Mice with Chemotherapy-Induced Alopecia." Journal of the National Cancer Institute. Dec. 19, 2001; vol. 93, No. 24, p. 1859, col. 1.
Maurer, et al. "Hair Growth Modulation by Topical Immunophilin Ligands." American Journal of Pathology. Apr. 1997; vol. 150, No. 4.
Altshuler, et al. "Extended Theory of Selective Photothermolysis." Lasers in Surgery and Medicine 29:416-432 (2001).

*Primary Examiner* — Christopher A Flory
*Assistant Examiner* — Jonathan Kuo
(74) *Attorney, Agent, or Firm* — Matthew S. Gibson; Reed Smith LLP

(57) ABSTRACT

The invention encompasses a method of inhibiting the growth of hair in skin including epilation of follicles in the skin, waiting until within 5 days of the commencement of metanagen, applying a photodynamic agent to the skin, and exposing the skin to photoactivating light.

8 Claims, No Drawings

METHOD FOR THE PERMANENT REMOVAL OF HAIR

RELATED APPLICATION

This application claims priority of U.S. patent application Ser. No. 61/698,976, entitled A METHOD FOR THE PERMANENT REMOVAL OF HAIR, filed Sep. 10, 2012, the entire disclosure of which is hereby incorporated by reference as if being set forth in its entirety herein.

FIELD OF THE INVENTION

This invention relates to the permanent or long term inhibition of hair growth.

BACKGROUND OF THE INVENTION

Hair is widely distributed in the skin. Hair is believed to serve a number of biological or physiological purposes. These include thermal protection, as well as protection from abrasion and from sun exposure. Hair also plays a role in sensory reception, most particularly the sense of touch. The appearance of hair also plays a role in visual signaling.

Humans have significantly less hair than other mammals, and its functions are commensurately reduced. However, the visual signaling role of human hair, sometimes referred to as aesthetic appearance, is undiminished.

Hair is part of a complicated anatomical structure that is sometimes referred to as the hair follicle. The hair shaft, which protrudes from the skin, is, for a practical purposes, the only portion of the hair follicle that is visible to the naked eye. However, there are additional structures in the hair follicle. Hair follicles consist of an in-folding of the surface of the skin that creates an opening, sometimes called a pore. This opening extends through several layers of the skin. It is lined with sheath cells and is typically associated with a sebaceous gland. The sebaceous gland secretes sebum, which serves to condition both the hair shaft and the surface of the skin. At the bottom of the follicle is the follicular bulb, which includes the follicular papilla, and these cells make up the portion of the follicle that are principally responsible for the generation of the hair shaft.

Hair follicles have long been known to undergo periodic cycles of activity. The first phase of this "hair cycle" is known as anagen, and is divided into six sub-phases. The first five sub-phases of anagen are collectively referred to as "proanagen," and the sixth sub-phase is referred to as "metanagen." Commencement of metanagen is characterized by the emergence of the hair shaft above the skin surface. Anagen is followed by successive stages in which the cells of the follicle becomes apoptotic, hair growth stops, and then the cycle is resumed and the hair-producing cells of the follicle again produce a hair shaft.

In addition to combing, trimming and coloring hair, humans often seek to remove hair over certain portions of their body. While the degree to which humans desire to remove some or all of their body hair varies significantly with age, gender and culture, hair removal is widely practiced.

Hair removal is sometimes classified as depilation (the removal of the hair shaft that protrudes from the surface of the skin) or epilation (removal of the entire hair shaft, including the portion below the skin) Depilation includes hair removal by shaving and also removal by use of chemical agents such as thioglycolate. Epilation can include mechanical removal of the hair shaft (e.g. plucking, waxing, sugaring), as well as laser treatment and electrolysis.

Most methods of hair removal have only a temporary effect. The hair grows back, sometimes within a day or two. Only a few methods of hair removal are permanent (i.e. inhibit the re-growth of the hair). For example, electrolysis treatments can permanently stop hair growth.

Permanent hair removal can be desirable in many circumstances. When persons are confident that they will not change their mind about having hair present on a particular portion of their body, permanent hair removal can be an attractive alternative to daily shaving or other hair removal techniques. Unfortunately, there are several serious drawbacks associated with all known methods of permanent hair removal.

Electrolysis is performed one hair at a time, making it an impractical technique for removal of hair from anything other than very small regions of the body. Electrolysis is also painful, sometimes too painful for the person to bear.

Infrared lasers can permanently remove hair, and can be applied to areas of skin, not just individual hairs. Unfortunately, infrared laser hair removal typically works by the absorption of the infrared laser energy by pigments in the hair shaft and associated follicular cells, which causes heating that is intended to kill the hair-generating cells. This cannot be accomplished in the case of lightly colored (e.g. blonde or red) or unpigmented (e.g. gray) hair. Pigmented skin tends to absorb the infrared laser energy in the same way that pigmented follicle cells do, which interferes with laser hair removal in persons with darkly or sometimes even moderately pigmented skin.

Infrared laser hair removal is also painful and typically requires repeated treatments in order to be effective.

There remains a need for an effective means of permanent hair removal that can be used efficiently, without excessive discomfort, and on all types and colors of hair.

Photodynamic therapy (PDT) is an established therapeutic method for certain disorders. PDT is characterized by the use of (1) a phototherapeutic agent and (2) light. The phototherapeutic agent is applied or provided to the tissue or organ of interest. The light is used to cause a photo-reaction (such as photoexcitation) in either the phototherapeutic agent, or in a metabolite of the phototherapeutic agent, or in a compound produced in response to the presence of the phototherapeutic agent (the activation reaction). This reaction results in a therapeutic effect.

Early phototherapeutic agents included porphyrins such as hematoporphyrin IX, hematoporphyrin derivative, or other such molecules, including Photofrin II.

The pioneering work of Kennedy & Pottier resulted in the discovery of the use of aminolevulinic acid (ALA) as a phototherapeutic agent. ALA is a precursor to a naturally occurring molecule—protoporphyrin IX. Exposing skin to light activates protoporphyrin IX in the skin. That is, the light excites or causes a reaction in the protoporphyrin IX molecule that results in the formation of reactive free radicals. Naturally occurring protoporphyrin IX can be activated by exposure to light, but occurs in quantities too small to cause any serious effect in normal tissue. By administering exogenous ALA, cells and tissues can be caused to produce greatly increased amounts of protoporphyrin IX. The resulting high concentrations of protoporphyrin IX can result in the generation of fatal quantifies of free radicals in the target cells/tissue when protoporphyrin IX is activated by exposure to light.

Kennedy & Pottier found that ALA-induced production of protoporphyrin IX made it possible to use PDT in the treatment of several disorders of metabolically active tissues. This technology has been used in the successful commercial product Levulan®, produced by Dusa Pharmaceuticals, and which has been approved by the U.S. FDA for the treatment of actinic keratoses.

PDT has long been thought to have some effect on hair growth. Some workers have reported that photo-dynamic therapy increases the growth of hair. Others have reported that PDT can inhibit hair growth. These workers report that effective inhibition of hair growth requires that the hair shaft be mechanically removed to create a clear opening in the pore of the follicle (unobstructed by the hair shaft) so that the photodynamic agent can penetrate the follicle and, when activated, destroy the hair-generating cells. See, for example, U.S. Pat. No. 5,669,916 to Anderson, and generally Altshuler et. al. "Extended Theory of Selective Photothermolysis" Lasers in Surgery and Medicine, Vol. 29, pp 416-432 (2001).

SUMMARY OF THE INVENTION

It has been discovered that hair can be permanently removed (that is, the hair producing function of the hair follicle can be permanently inhibited) by mechanical epilation followed by PDT at about the time of commencement of metanagen.

Without wishing to be bound by any particular theory of operation, it is believed that the mechanical epilation causes a significant increase in the metabolic activity of the hair-generating cells in the follicle, thereby making them susceptible to destruction by PDT.

It has been found that, contrary to the understanding in the art, removal of the hair shaft from the pore to provide a clear opening for the photodynamic agent does not result in a consistently effective inhibition of hair growth. Even Anderson reported that this technique has a failure rate of up to 50%.

Instead, more effective inhibition of hair regrowth can be achieved by use of PDT when the hair-producing cells of the follicle are in a highly active metabolic state, and that this highly active metabolic state can be triggered by the mechanical removal of the hair shaft, and occurs at about the commencement of metaangen (the emergence of the hair shaft from the pore after mechanical removal of the hair.) Variations in the time to commencement of metaangen between various locations on the body are well known to workers in the field. The emergence of the hair shaft from the pore (commencement of metanagen) can be readily observed even by a lay person, making it easy to identify this time at any particular place on any particular patient. This highly active metabolic state often arises within 2 or 3 days to a week or 10 days after the mechanical removal of the hair shaft. By about the time of metanagen, a new hair shaft is well along in its regeneration, and usually has plugged or obstructed the pore (exactly what the prior art believed should be avoided). Generally, PDT should be applied within 5 days of the commencement of metanagen, but can be done within a week to 10 days of the commencement of metanagen. Application of PDT within 3 days of commencement of metanagen, and especially within 3 days after commencement of metanagen is preferred. Thus, the understanding of the prior art that PDT should be used to permanently inhibit hair growth only when the pore does not contain a hair shaft has been found to be incorrect.

DETAILED DESCRIPTION OF THE INVENTION

Any known photodynamic agent can be used in this invention, including ALA. Derivatives of ALA, including alkylated derivatives of ALA, can also be used in the treatment method of this invention. These include $C_1$ to $C_8$ alkyl derivatives of ALA such as methyl ALA and hexyl ALA.

Topical formulations suitable for use in ALA-based PDT are well known in the art. These include ALA and its pharmaceutically acceptable salts, such as ALA hydrochloride and sodium ALA. Any topical vehicle that delivers ALA to the skin so that it can be taken up by the follicle can be used. Levulan® ALA is a formulation that is commercially available and suited to use in this invention.

The concentration of ALA in the topical formulation can range from 1 to 30 percent. Concentrations within this range can be selected on the basis of the volume of the formulation to be applied, the size of the affected nail, the extent of the infection, and other clinical factors well known to practitioners, and well within the scope of good clinical judgment. Concentrations in the range of 5 to 20 percent are most useful, within 20 percent ALA being particularly useful.

The ALA can be applied to the skin by any of the conventional application techniques known in the art, such as swabs, brushes, cotton balls, gauze pads or the like. The Kerastick® applicator sold by DUSA Pharmaceuticals can also be used.

Light sources suitable for use in ALA-based PDT are also well known and generally available. The wavelengths of light that are capable of penetrating the skin and exciting the protoporphyrin IX molecule are well known to those skilled in the art. Devices capable of providing such light are also readily available. These include the BLU-U® illuminator, sold by DUSA Pharmaceuticals, and the Sciencetech (London, Ontario, Canada) Model 7500 PDTI (Photodynamic Therapy Illuminator), which emits red light in the 600-650 nm wavelength range. Laser light at wavelengths that excite the protoporphyrin IX molecule may also be used, although it should be noted that these wavelengths are typically different than those used in the conventional laser hair removal mentioned above.

EXAMPLE 1

A healthy volunteer subject with Fitzpatrick's type II skin and light colored hair was treated with PDT on the anterolateral thigh. At the baseline visit, a suitable target area on the anterolateral thigh was identified and catalogued identified using a leg diagram and microtattoos. A subjective assessment of hair density and a baseline hair count were performed for the test site. Wax epilation of the target area was performed using a commercially available cold waxing system. Remaining residual hairs were removed with forceps under magnification. The subject was instructed not to depilate (chemical or shaving) or epilate the target area and to return for PDT treatment in 10 days.

A subjective assessment of the target site was made prior to application of ALA. Light "stubble" evidencing hair re-growth was noted in the target area which was otherwise unremarkable. Levulan Kerastick, 20%, for Topical Solution was applied to the target area and allowed to incubate for a total of 4 hours prior to light exposure. One hour after Levulan application, the test site was wiped with an isopropyl alcohol wipe and allowed to dry. The subject was advised to cover the test site with light protective clothing and to not expose the treatment site to bright light during the entire incubation interval.

At the complete of the incubation interval, the target area was exposed to 300 $J/cm^2$ of red light from the Sciencetech Model 7500 PDTI. Evaluation of the PDT response of the target area and subjective evaluation of subject discomfort was made immediately after the light treatment at which time it was noted that the target skin area appeared slightly red and edematous. The subject reported moderate burning and stinging during light therapy which subsided shortly after the cessation of light delivery.

The subject was followed at 1, 3, and 6 months post light exposure. Subjective assessments were made at all follow up visits while hair counts were done only at 3 and 6 months. Redness in the target area was noted at the 1 month visit which as resolved by month 3. At the 6 month follow visit, hair counts in the target area were less than 30% of the baseline value.

EXAMPLE 2

A healthy volunteer subject with Fitzpatrick's type III skin and light brown colored hair was treated with PDT on the anterolateral thigh. At the baseline visit, a suitable target area on the thigh was identified and catalogued identified using a leg diagram and microtattoos. A subjective assessment of hair density and a baseline hair count were performed for the test site. Wax epilation of the target area was performed using a commercially available cold waxing system. Remaining residual hairs were removed with forceps under magnification. The subject was instructed not to chemically depilate or shave or epilate the target area and to return for PDT treatment in 10 days.

A subjective assessment of the target site was made prior to application of ALA. Dark stubble was noted in the target area, but the target area was otherwise unremarkable. Levulan Kerastick, 20% was applied to the target area and allowed to incubate for a total of 3 hours prior to light exposure. One hour after Levulan application, the test site was wiped with an isopropyl alcohol wipe and allowed to dry. The subject was advised to cover the test site with light protective clothing and to not expose the treatment site to bright light during the entire incubation interval.

At the complete of the incubation interval, the target area was exposed to 200 J/cm$^2$ of red light from a Coherent NOVA 9000 Argon Pumped Dye Laser. Light from the laser was provided to the target area using a microlens fiber. The laser power was adjusted to illuminate the target at a power density of 120 mW/cm$^2$. Evaluation of the PDT response of the target area and subjective evaluation of subject discomfort was made immediately after the light treatment at which time it was noted that the target skin area appeared red and edematous. The subject reported a sharp burning sensation and stinging during light therapy.

The subject was followed at 1, 3, and 6 months post light exposure. Subjective assessments were made at all follow up visits while hair counts were done only at 3 and 6 months. Redness in the target area was noted at the 1 month visit which gradually resolved by month 6. At the 6 month follow visit, hair counts in the target area were less than 25% of the baseline value.

The invention claimed is:

1. A method of inhibiting the growth of hair in skin, comprising the steps of:
   epilation of follicles in the skin,
   waiting until within 10 days after emergence of a hair shaft from a pore in the follicles subjected to epilation,
   applying a photodynamic agent to the skin, and
   exposing the skin to photoactivating light,
   wherein the photoactivating light is emitted from an illuminator device, and wherein the
   photoactivating light consists solely of red light in the 600-650 nm wavelength.

2. The method of claim 1, wherein the epilation of follicles in the skin is performed by mechanical removal of a hair shaft from the follicle.

3. The method of claim 2, wherein the waiting period is until within 3 days after emergence of the hair shaft from the pore.

4. The method of claim 1, wherein the photodynamic agent is selected from the group consisting of aminolevulinic acid and its pharmaceutically acceptable salts.

5. The method of claim 1, wherein the photodynamic agent is selected from the group consisting of 20% solution of aminolevulinic acid and its pharmaceutically acceptable salts.

6. The method of claim 1, wherein the waiting period is until within 5 days after emergence of the hair shaft from the pore in the follicles subjected to epilation.

7. The method of claim 2, wherein the waiting period is until within 5 days after emergence of the hair shaft from the pore in the follicles subjected to epilation.

8. The method of claim 1, wherein the waiting period is until within 3 days after emergence of the hair shaft from the pore in the follicles subjected to epilation.

* * * * *